(12) United States Patent
Kilcoin et al.

(10) Patent No.: US 8,716,006 B2
(45) Date of Patent: May 6, 2014

(54) MULTI-CHAMBER ROTATING VALVE

(75) Inventors: Christopher Kilcoin, Boulder Creek, CA (US); Konstantin Aptekarev, Santa Cruz, CA (US); Richard S. Murante, Rochester, NY (US); Dennis M. Connolly, Rochester, NY (US)

(73) Assignee: Integrated Nano-Technologies, LLC, Henrietta, NY (US)

( * ) Notice: Subject to any disclaimer, the term of this patent is extended or adjusted under 35 U.S.C. 154(b) by 393 days.

(21) Appl. No.: 12/754,205

(22) Filed: Apr. 5, 2010

(65) Prior Publication Data

US 2010/0252116 A1 Oct. 7, 2010

Related U.S. Application Data

(60) Provisional application No. 61/166,519, filed on Apr. 3, 2009.

(51) Int. Cl.
  C12M 1/34 (2006.01)
  C12M 3/00 (2006.01)
  C12M 1/00 (2006.01)
  B05B 7/00 (2006.01)
  F16K 31/00 (2006.01)

(52) U.S. Cl.
  USPC ......... 435/287.2; 435/287.1; 435/283.1; 239/61; 239/62; 251/292

(58) Field of Classification Search
  USPC ......... 435/287.2, 283.1–309.4; 239/61, 62; 251/292
  See application file for complete search history.

(56) References Cited

U.S. PATENT DOCUMENTS

| | | | |
|---|---|---|---|
| 4,068,528 A | 1/1978 | Gundelfinger | |
| 4,702,889 A | 10/1987 | Cabrera | |
| 4,889,692 A | 12/1989 | Holtzman | |
| 5,105,851 A | 4/1992 | Fogelman | |
| 5,524,496 A | 6/1996 | Nagai | |
| 5,558,838 A | 9/1996 | Uffenheimer | |
| 6,129,828 A | 10/2000 | Sheldon | |
| 6,374,684 B1 | 4/2002 | Dority | |
| 6,769,573 B1 | 8/2004 | Kazarian et al. | |
| 8,230,774 B1 * | 7/2012 | Hunte | 99/289 R |
| 2004/0157343 A1 | 8/2004 | Sandell | |
| 2005/0282202 A1 | 12/2005 | rolaski | |
| 2006/0177844 A1 * | 8/2006 | Ching et al. | 435/6 |

(Continued)

FOREIGN PATENT DOCUMENTS

| | | |
|---|---|---|
| WO | WO85/04719 | 10/1985 |
| WO | WO00/25924 | 5/2000 |

OTHER PUBLICATIONS

International Searching Authority, International Search Report and Written Opinion in PCT No. PCT/US2010/029961, Mailed Nov. 11, 2010.

(Continued)

*Primary Examiner* — Nathan Bowers
*Assistant Examiner* — Lydia Edwards
(74) *Attorney, Agent, or Firm* — Hiscock & Barclay, LLP

(57) ABSTRACT

A fluid delivery system having a rotating reservoir insert and a cartridge body. The rotating reservoir insert having a plurality of reservoirs in communication with ports on the external surface of the insert. The ports are positioned such that upon rotation the port is in-line with a fluid extracting device, such as a syringe, capable of extracting fluid from the reservoir.

15 Claims, 25 Drawing Sheets

(56) References Cited

U.S. PATENT DOCUMENTS

2007/0092876 A1 4/2007 Xu
2007/0244314 A1 10/2007 Mori
2008/0102493 A1 5/2008 Ongenga et al.

OTHER PUBLICATIONS

Zheng et al., "Bioseparation Techniques and Their Applciations," in Cseke et al., Handbook of Molecular and Cellular Methods, 2nd ed. (New York, CRC Press, 2004), 25 pages.

* cited by examiner

Rectangular Configuration

Rectangular

Constant Radial, Variable ID
Configuration

Constant Radial, Variable ID

Variable Radial, Constant ID
Configuration

Variable Radial, Constant ID
Max Disp – .00132 mm
Max Stress- 7.6 psi

MULTI-CHAMBER ROTATING VALVE

CROSS-REFERENCE TO RELATED APPLICATIONS

This application claims priority from U.S. Provisional Patent Application Ser. No. 61/166,519, filed Apr. 3, 2009, the contents of which are incorporated in their entirety by reference.

FIELD OF THE INVENTION

The present invention relates to multi-chamber valves, and more particularly to multi-chamber rotating valves. The invention further relates to a method for transmitting a plurality of fluids from storage reservoirs to a reaction chamber.

BACKGROUND OF THE INVENTION

Fluid analysis generally requires a series of process steps. Theses process steps generally require that distinct fluids contact a reaction area at different times and in varying secession. Furthermore, each fluid may require different pre-treatment prior to contacting the reaction area such as chemical, optical, thermal, mechanical, magnetic or acoustical pre-treatment steps. A single fluid sample may be subjected to a variety of pre-treatment steps prior to contact with a reaction area such as heating or ultrasonic processing. As the number of fluids and pre-treatment steps increase the more complex the fluid delivery system becomes.

Present designs for fluid delivery systems are customized for a particular process and are not easily converted to new processes. Generally, fluid delivery systems comprise a series of chambers uniquely configured for pre-treating and delivering a particular fluid. These systems are not easily adaptable to new pre-treatment steps or fluid delivery without changing both the chambers and delivery procedure.

Therefore, there is a need for a fluid delivery system that is easily configurable to new delivery procedure and pre-treatment steps.

Further, there is a need for a disposable fluid delivery system that can be easily inserted and removed from a bench-top or portable device.

Yet further, there is a need for a fluid delivery system that is easily manufactured and customizable to suit varying fluid delivery needs.

SUMMARY OF THE INVENTION

The present invention provides an apparatus and method for transmitting a plurality of fluids. A rotating valve comprising a rotating reservoir insert having a plurality of reservoirs is situated within a cartridge body. The rotating valve contains reservoirs for containing fluid' chambers for pre-treating fluid; a plurality of fluid paths for connecting the reservoirs and chambers to external ports; and pass-through channels for transmitting fluids.

The use of a rotating design allows for a single plunger to draw and push fluid samples without the need for a complex valve system to open and close at various times. This greatly reduces potential for leaks and failure of the device. Furthermore, the use of a plunger allows for greater configurability in adjusting the amount of fluid drawn.

The reservoir insert is injected molded allowing for varied configurations with minimal costs. The exterior of the reservoir insert is cylindrical to allow free rotation about its axis when encased in the cartridge body. The interior section of the reservoir insert can be modified to include any size or shape reservoir or pre-treatment chamber.

Customized rotating valves retain the same exterior shape and dimensions and can be inserted into existing equipment. The processing protocol of the instrument is easily modified to account for any new chambers, sample sizes, processing times, or port locations.

The rotating valve can be stored in position leaving all ports and vents closed allowing for long-term storage and shipping of the rotating valve with liquid and solid reagents loaded within the valve.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION

The rotating valve of the instant invention is a two piece construction capable of various positioning to allow the passage of fluid contained in the reservoirs into the fluid paths. The two piece design allows for easy manufacturing and assembly. The design further allows for the rotating valve to be a disposable piece in instruments requiring a plurality of fluids. In one embodiment, the rotating valve is a single use piece for use in detection devices. The rotating valve contains the necessary fluids for biological testing and further is capable of being injected with a field sample.

Figure 1A:
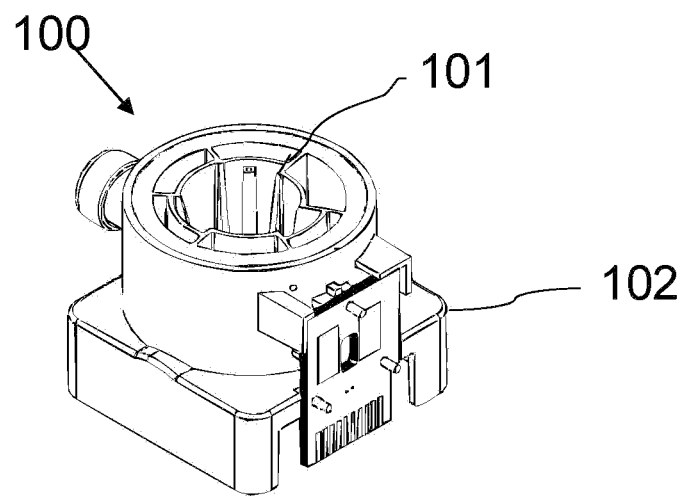
FIGS. 1A-1B show a graphical representation of a rotating valve according to one embodiment.
Figure 1B:
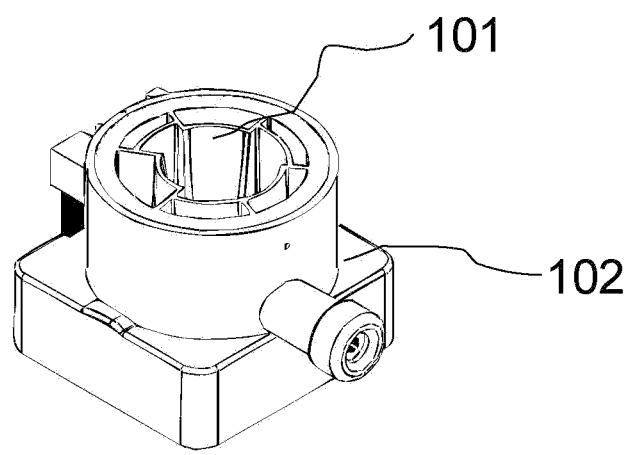

Referring to FIGS. 1A-1B there is shown an assembled rotating valve of the instant invention. The rotating valve comprises two main components. The reservoir insert 101 is contained within the cartridge body 102. The rotating valve 100 is a disposable component containing a plurality reservoirs capable of storing a plurality of fluids. In one embodiment, the reservoir insert 101 and the cartridge body 102 are both formed through injection molding techniques.

In one embodiment a chip containing biological probes is affixed to the cartridge body 102. The fluid contained in the reservoirs is transferred to contact the chip containing biological probes initiating reaction or detection chemistry. The chip is in communication with a detection device such as a bench-top or portable detection device to indicate the presence of target biological probes in any sample. The rotating valve 100 is inserted into a detection device that is in electrical communication with the chip. The detection device further affixes the cartridge body 102 into a fixed position.

Figure 2:
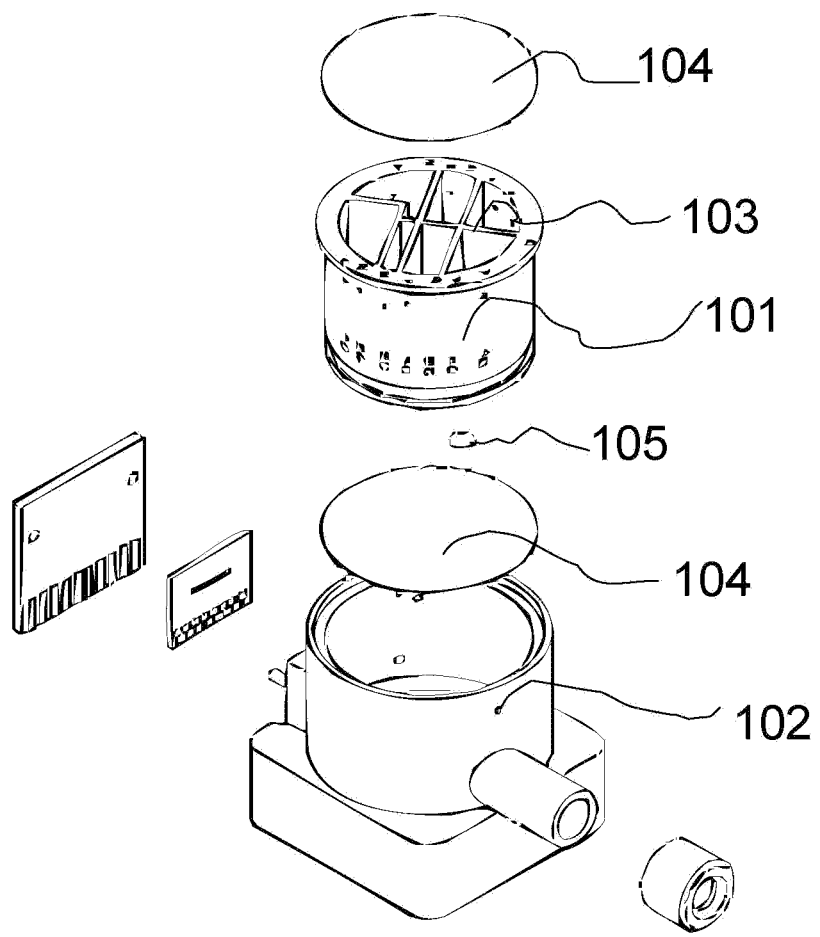
FIG. 2 shows an expanded view of a rotating valve according to one embodiment.

Referring to FIG. 2 there is shown an exploded view of the instant invention. The reservoir insert 101 is capable of containing a plurality of fluids in the various reservoirs 103. The heat seal films 104 seal the fluids into the reservoir insert and prevent leaks while allowing for the injection of samples. The heat seal films 104 seal the reservoirs from the outside environment. The heat seal films 104 further allow for fluid to be added to or removed from the reservoirs without compromising the integrity of the seal. In one embodiment, the heat seal films 104 improve energy transfer into and out of the reservoirs and chambers of the reservoir insert 101. Energy transfer includes but is not limited to heat, ultrasonic and magnetic. Optionally, a filter 105 is placed in-line with particular fluid paths to filter large solids from the fluid. In one embodiment Once the heat seal films 104 are sealed onto the reservoir insert 101 the reservoir insert 101 is affixed to the cartridge body 102. In one embodiment, the reservoir insert 101 "snaps into" the cartridge body 102. It is understood that the heat seal films 104 can be sealed to the reservoir insert 101 after the reservoir insert 101 is affixed to the cartridge body 102.

Figure 3A:
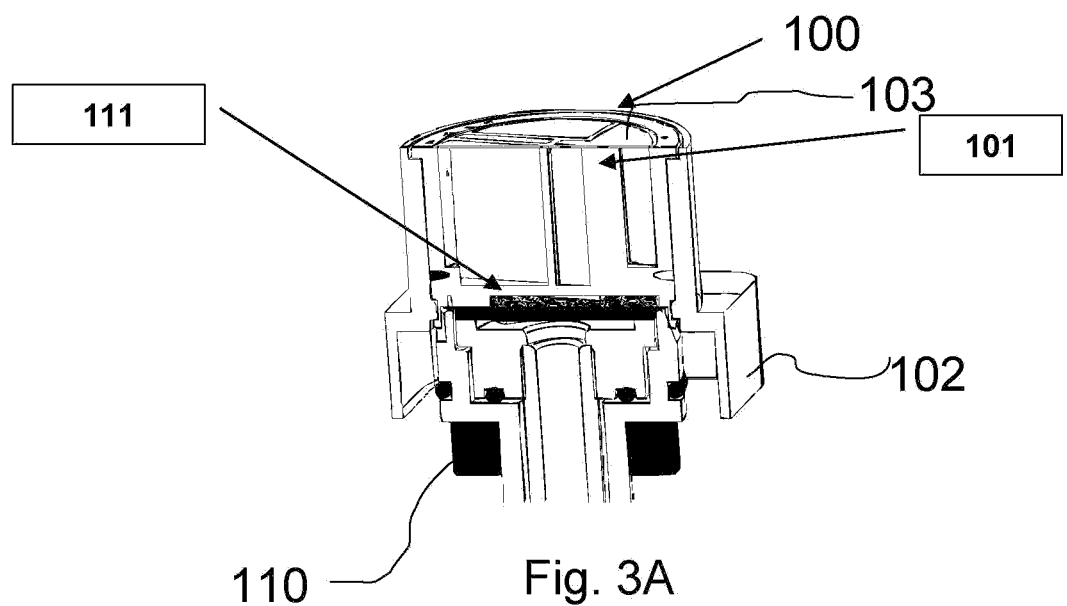
FIG. 3A shows a cross-sectional view of a rotating valve according to one embodiment.
Figure 3B:
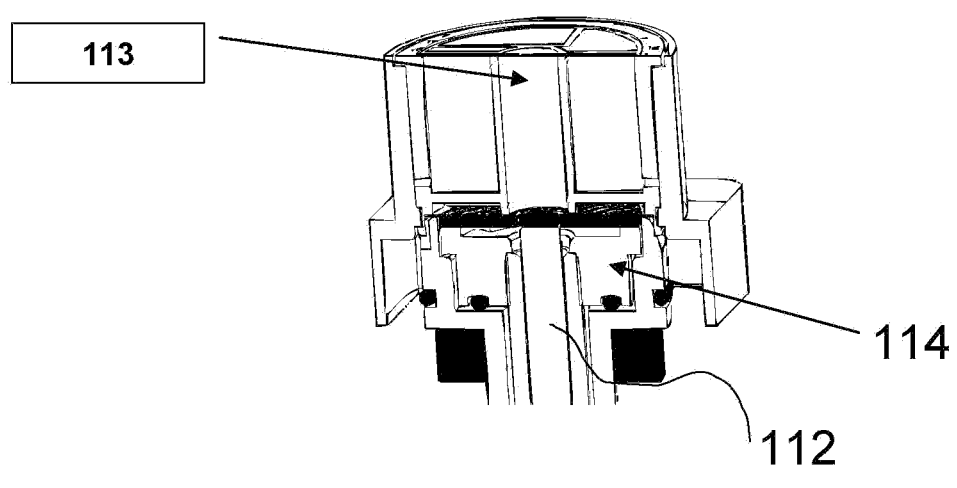
FIG. 3B shows a cross-sectional view of a rotating valve according to one embodiment having an electromagnet and sonicator built into the valve.
Figures 4A, 4B:
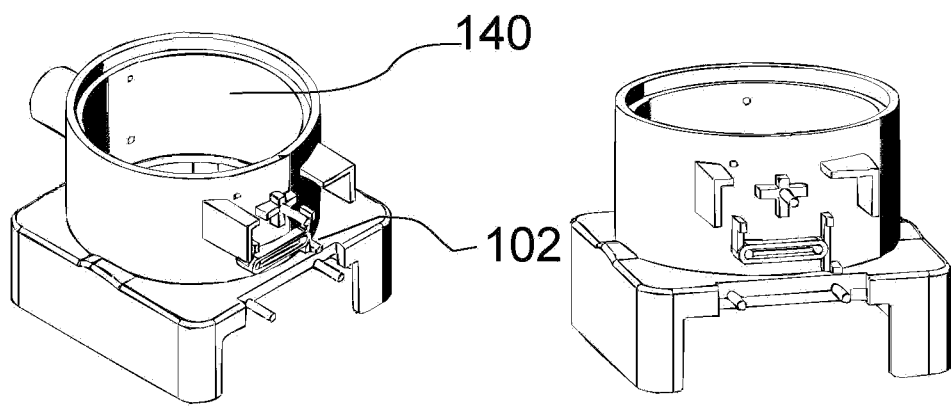
FIGS. 4A-4D show a graphical representation of the cartridge body according to one embodiment.
Figures 4C, 4D:
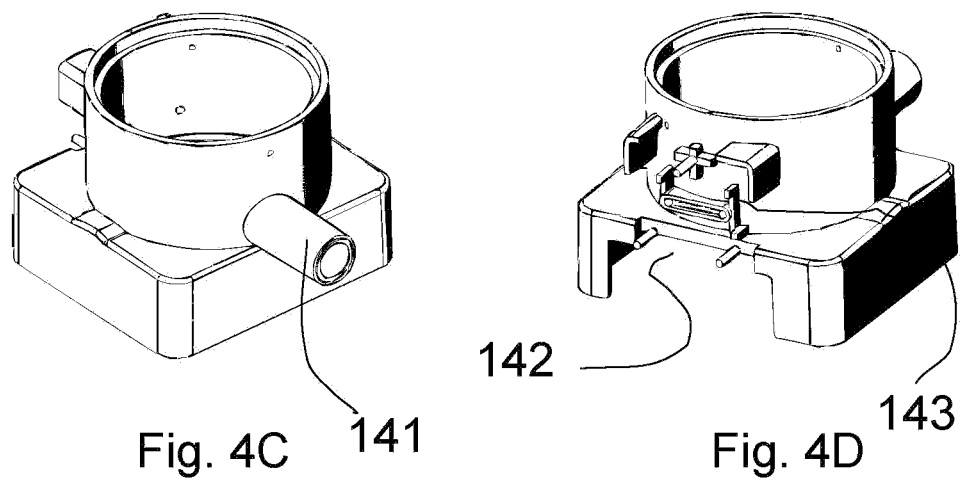

Referring now to FIGS. 3A-3B there is shown a cross sectional view of the rotating valve 100. The rotating valve 100 is set onto a drive mechanism 110. The drive mechanism 110 is capable of rotating the reservoir insert 101 to the desired configuration. The drive mechanism 110 rotates the reservoir insert 101 while the cartridge body 102 remains stationary. In one embodiment the drive mechanism has an optional heater 111. The heater is capable of heating the fluids contained in the reservoirs 103 to the desired temperature. Alternatively, heating chambers are strategically positioned above the heater to heat the fluid in the chamber without significantly heating the fluids in the reservoirs 103. In one embodiment, the heat film seals 104 facilitate this heating without significantly heating the fluids in the reservoirs 103. Treatment chambers are incorporated into the reservoir insert 101 to facilitate mixing, heating, disrupting, pressurization or any other treatment process.

In one embodiment the drive mechanism has a disruptor 112. The disruptor is capable of mixing or breaking down the fluids contained in the reservoirs 103 by applying an ultrasonic force. Alternatively, the rotating valve has a disrupting chamber 113 for mixing fluids in a chamber distinct from the reservoirs. In one embodiment small beads are located in the disrupting chamber or reservoir to assist in mixing fluids or breaking down samples. The disrupter 112 applies an ultrasonic force causing the beads to become excited and move through the fluid. In one embodiment a magnet 114 is utilized to generate an electric field. The magnet can pull or push magnetic particles in the reservoir insert. The magnet 114 can concentrate a sample of magnetic particles or speed up the diffusion process by guiding any magnetic particles.

Referring to FIGS. 4A-4D there are shown various views of one embodiment of the cartridge body 102. It is understood that various designs can be used to house the reservoir insert. The cartridge body 102 has an inner cylindrical surface 140. The inner cylindrical surface 140 houses the reservoir insert (not shown). The inner cylindrical surface 140 is smooth to allow the reservoir insert to freely rotate. The cartridge body is constructed from any material that is both ridged enough to support the cartridge body and smooth enough to allow for rotation of the reservoir insert. In one embodiment, the inner cylindrical surface 140 has a slight taper to facilitate attachment of the reservoir insert (not shown) having an outer cylindrical surface with a slight taper.

In one embodiment the cartridge body has a syringe molding 141. Although only one syringe is shown it is understood that a plurality of syringes can be used. The syringe molding 141 is capable of housing a plunger. The phinger draws and pushes fluids through the reservoir inserts fluid paths. In one embodiment the plunger 144 is retained within the syringe molding 141. Optionally, the cartridge body has a reaction chamber 142 and sensor mount 143. The sensor mount 143 is capable of holding a sensor board. The sensor board is aligned to the sensor mount 143 by the alignment posts 146. The plunger delivers fluids through the fluid paths and to the reaction chamber 142. The fluids chemically react with other fluids or devices in communication with the reaction chamber 142. It is understood that a fluid output can be attached to the cartridge body to allow the fluid to transfer from the rotating valve to a desired location. Furthermore, a fluid input allows the introduction of fluids to the rotating valve.

In one embodiment the sensor board contains a chip having a reactive surface. The chip is positioned such that it is in communication with the reaction chamber 142. In one embodiment the chip forms one side of the reaction chamber 142. Fluid flows into the reaction chamber 142 and contacts the reactive surface of the chip (not shown). The chip is in electrical communication with a detection device to provide readings and results of the testing.

Figure 5A:
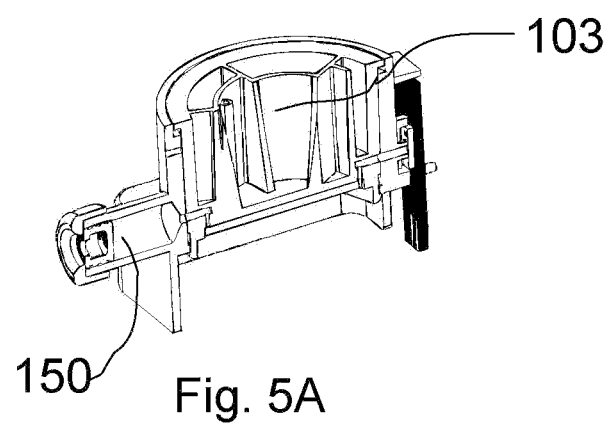
FIGS. 5A-5B show a cross-sectional view of an assembled rotating valve according to one embodiment having the multi-chamber reservoir secured in the cartridge body.
Figure 5B:
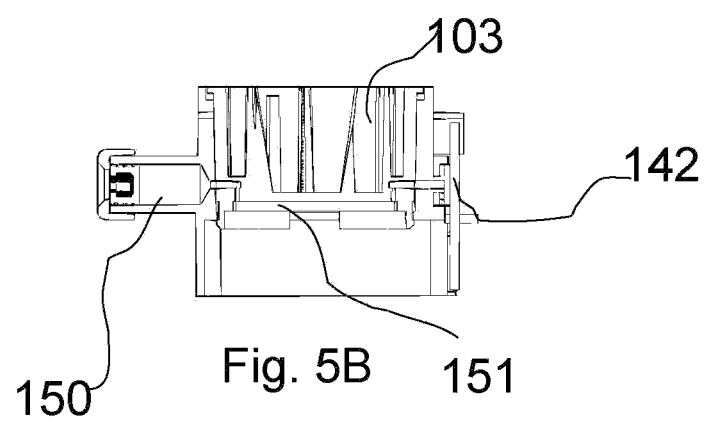
Figure 6A:
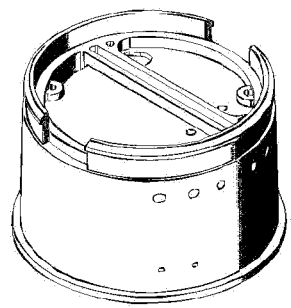
FIGS. 6A-6G show a graphical representation of the multi-chamber reservoir according to one embodiment.
Figure 6B:
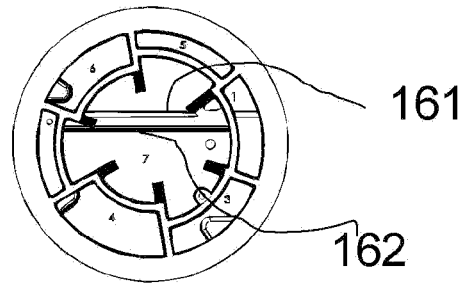
Figure 6C:
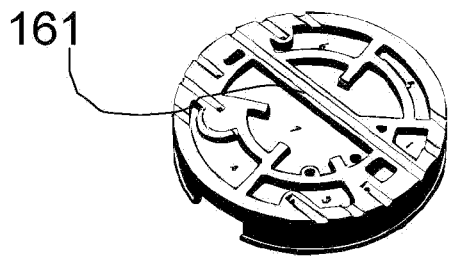
Figure 6D:
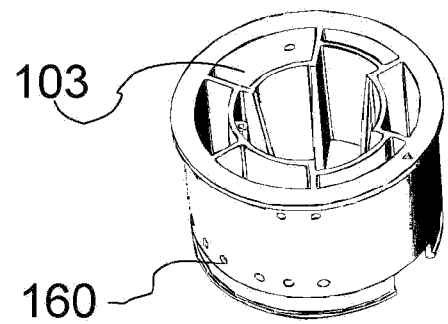
Figure 6E:
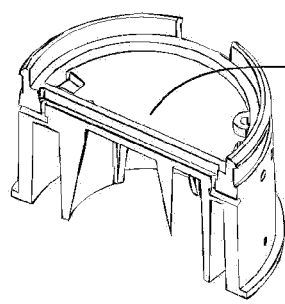
Figure 6F:
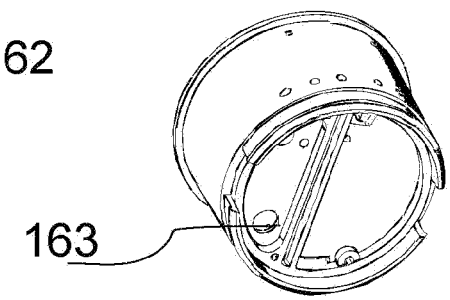
Figure 6G:
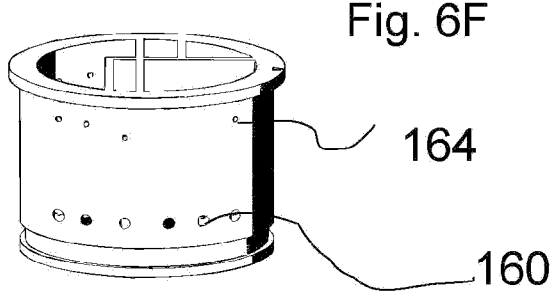

Referring to FIGS. 5A-5B there is shown a cross sectional view of an assembled rotating valve having a plunger 150. The plunger 150 is capable of drawing fluid from the reservoirs 103. Once the plunger 150 draws the fluid, the rotating valve repositions the fluid path to align a distinct port with the syringe molding. The plunger 150 then pushes the fluid through the fluid path 151 into the reaction chamber 142, a different reservoir, or a pre-treatment chamber.

Referring to FIGS. 6A-6G there are shown multiple views of the reservoir insert. The reservoir insert has an outer cylindrical surface 106. In one embodiment the outer cylindrical surface 106 is tapered. The reservoir insert contains multiple reservoirs 103. The reservoirs 103 can contain samples, standards, wash, catalyst or any other desirable fluid. In one embodiment the reservoirs 103 include a waste reservoir to discharge fluids. The reservoir insert further contains multiple ports 160. Each port 160 has a unique fluid path. Each chamber and reservoir has a fluid path that is in communication with a port to transfer fluid to or from the chamber or reservoir. A syringe molding on the cartridge body (not shown) lines up with a port to extract or push fluid. To prevent pressure differentials from forming pressure relief ports 164 are positioned along the reservoir insert. In addition to the unique fluid paths, the reservoir insert contains at least one fluid through channel 161. The fluid through channel 161 allows for the fluid to flow from the one end of the reservoir insert to the other. For example, the fluid can flow from the syringe molding to the reaction chamber of the cartridge body (not shown).

To prevent fluid interaction in the fluid through channel 161 a plurality of fluid through channels are used. The secondary fluid through channel 162 is used to prevent early reactions or other adverse fluid interactions. In one embodiment the reservoir insert contains a heater contact region 163. The heater contact region is positioned below the reservoirs for which it is desirable to heat the fluid in the reservoir. Furthermore, the heater is capable of heating the fluid through channel 161.

Figure 7A:
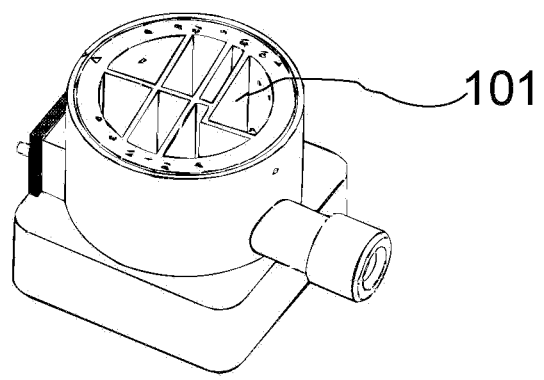
FIGS. 7A, 7B, 8A, 8B, 9A, 9B, 10A, 10B, 11A, 11B, 12A, 12B, 12C, 13A, 13B, 14A, 14B, 14C, 15A, 15B, 16A, 16B and 16C show various graphical representations of an assembled rotating valve with the multi-chamber reservoir positioned for desired fluid flow through the channels according to one embodiment.
Figure 7B:
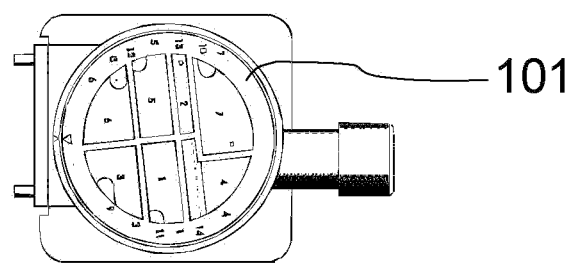

Referring to FIGS. 7A-16C there are shown multiple of views of an assembled rotating valve rotated in various positions. As shown in FIGS. 7A-7B the reservoir insert 101 is in a closed position. No ports are in line with the syringe molding (not shown). This prevents any leakage of fluid from the reservoir. In one embodiment at least one reservoir is a sample reservoir. The sample reservoir enables the user to inject a fluid sample into the reservoir through the heat film seal. In one embodiment the sample reservoir contains disrupting objects, such as glass beads, to assist in breaking down samples into testable nucleic acid strands.

Figure 8A:
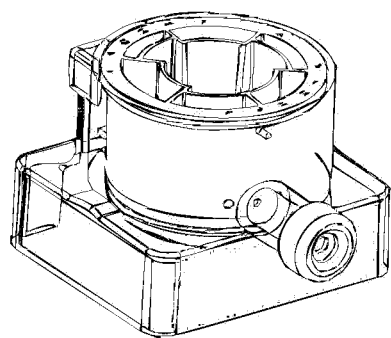
Figure 8B:
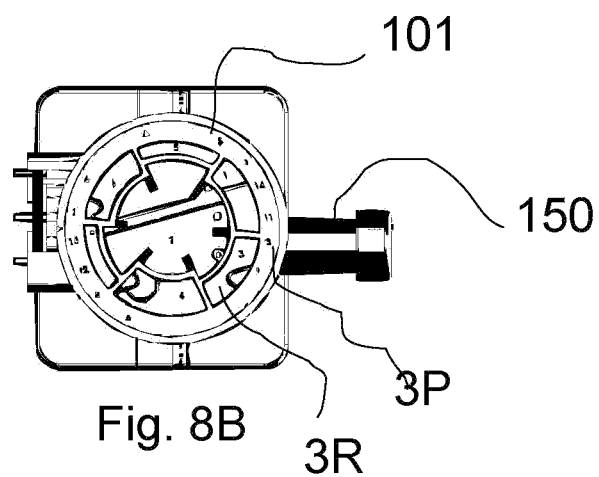
Figure 9A:
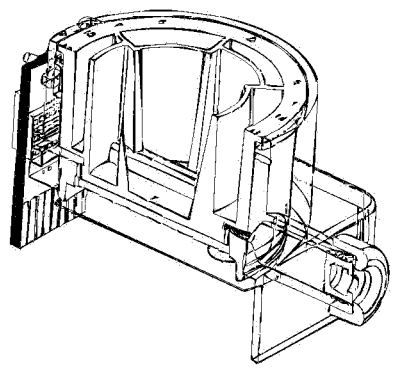
Figure 9B:
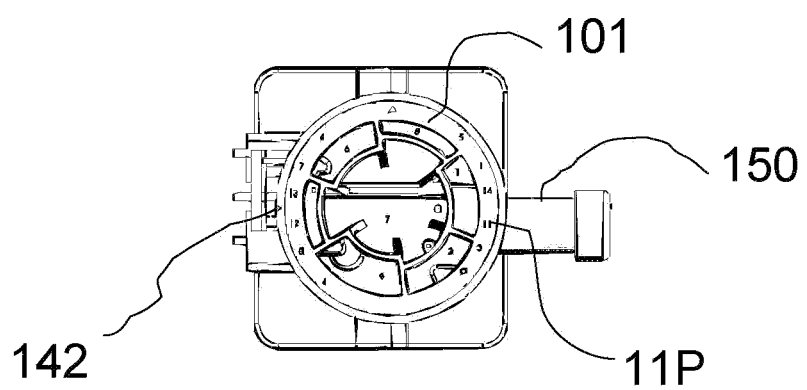

Referring to FIGS. 8A-8B the reservoir insert 101 is positioned such that port 3 is in-line with the syringe molding. Once positioned fluid from reservoir 3 can be drawn through port 3 and into the syringe molding 141. Once fluid is pulled from a reservoir, and no additional fluid is required from that reservoir, that reservoir can be used as an alternative reservoir for waste storage. Referring to FIGS. 9A-9B, the reservoir insert 101 is positioned such that port 11 is in-line with the syringe molding. The plunger pushes the fluid drawn from reservoir 3 into port 11 and the fluid passes to the reaction chamber 142.

Figure 10A:
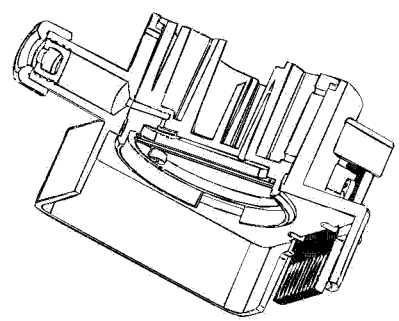
Figure 10B:
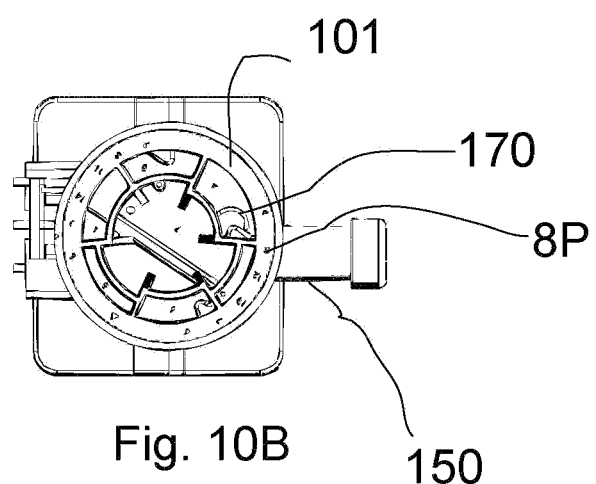
Figure 11A:
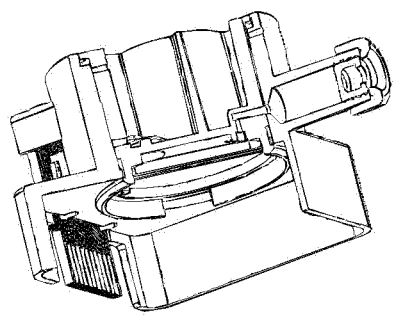
Figure 11B:
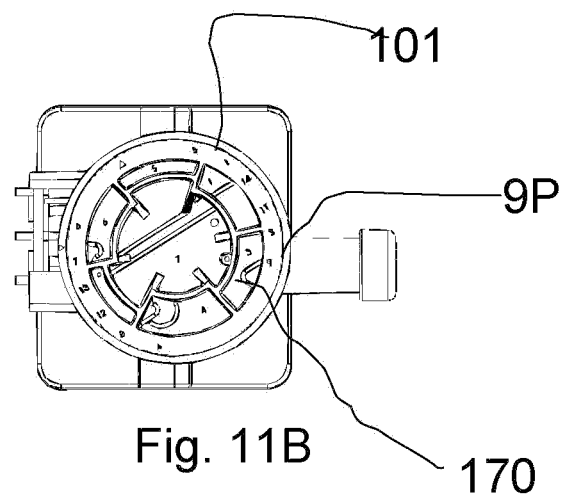

Referring to FIGS. 10A-10B the reservoir insert 101 is positioned such that port 8 is in-line with the syringe molding. In one embodiment fluid is pushed from the syringe molding 141 into port 8 and into a heating chamber. Once in the heating chamber 170 the fluid is heated at the desired temperature for a predetermined amount of time. Once the heating has completed the fluid is drawn back into the syringe molding. It is understood that the fluid may be drawn through the same port 8 or unique port in communication with the heating chamber. As shown in FIGS. 11A-11B the fluid is drawn into the syringe molding from a unique port 9 in communication with the heating chamber 170.

Figure 12A:
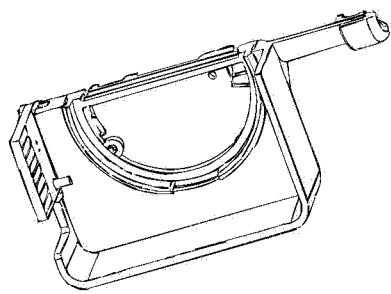
Figure 12B:
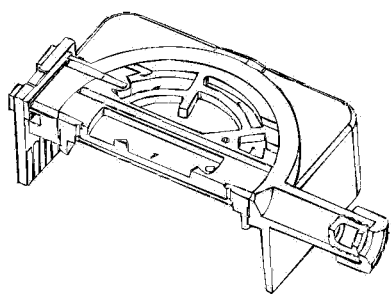
Figure 12C:
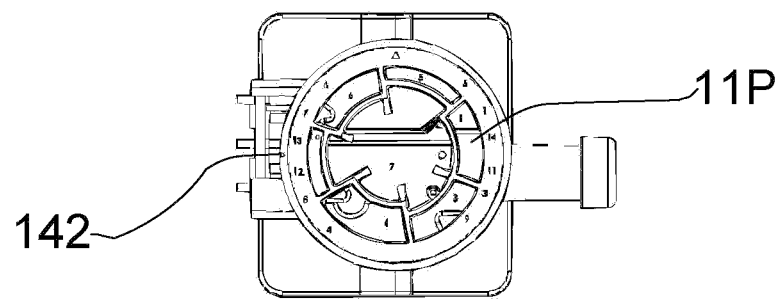

Referring now to FIGS. 12A-12C there is shown the flow through fluid path 161 from the syringe molding to the reaction chamber 142. In this embodiment the flow through fluid path corresponds with port 11.

Figure 13A:
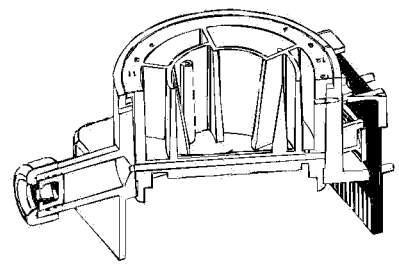
Figure 13B:
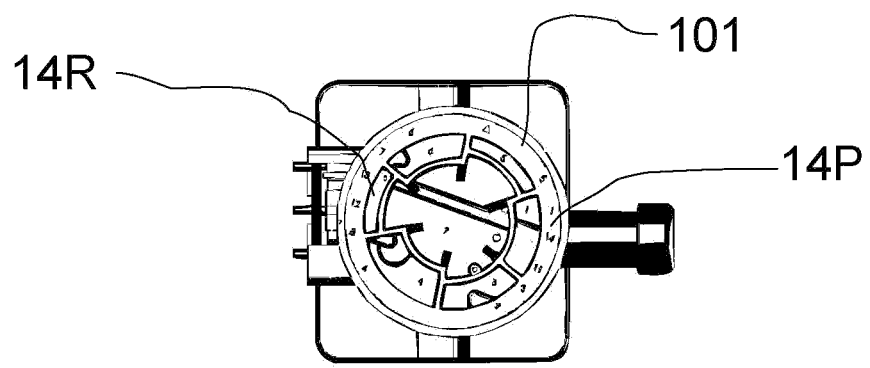
Figure 14A:
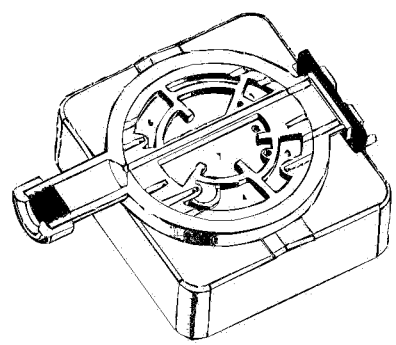
Figure 14B:
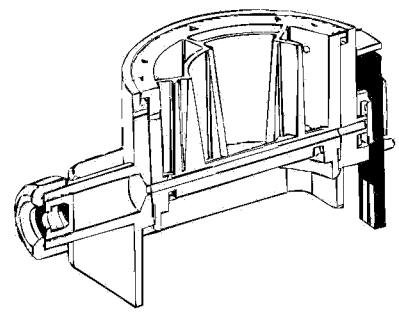
Figure 14C:
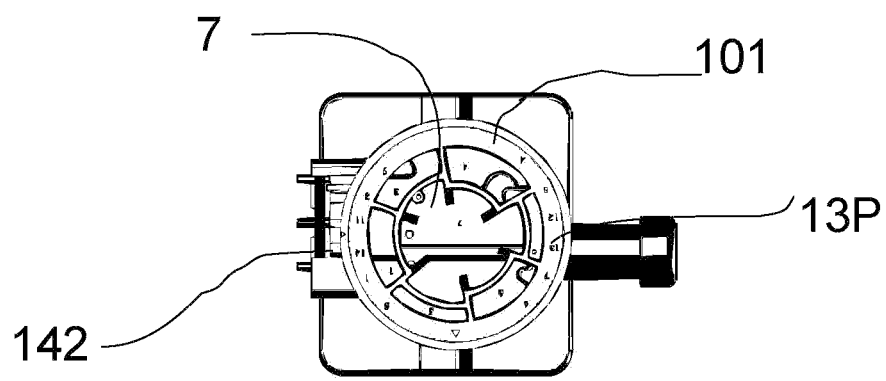

Referring to FIGS. 13A-13B there is shown the reservoir insert 101 positioned such that port 14 is in-line with the syringe molding. Reservoir 14 is in communication with port 14. The fluid contained in reservoir 14 is pulled into the syringe molding. The reservoir insert 101 then rotates to port 13 as shown in FIGS. 14A-14C. The fluid from reservoir 14 is then pushed through port 13 to the reaction chamber 142. The fluid passes through a channel that is distinct from the channel associated with port 11. This prevents fluids from coming in contact with and reacting with each other while in the channels. The fluids first come into contact in the reaction chamber 142.

After the desired reaction time the plunger pushes the fluid from the reaction chamber 142 into the waste reservoir 7. The plunger draws the fluid back through port 11 and the reservoir insert rotates to a port in communication with waste reservoir 7. The plunger then pushes the fluid into the waste reservoir 7. It is understood that after use any reservoir can be utilized as a waste reservoir. In an alternative embodiment, the plunger stops pushing fluid once it reaches the reaction chamber 142. Upon completion of the reaction time, the plunger continues to push the fluid through the reaction chamber and into a port in communication with a waste reservoir or separate archive reservoir. An archive reservoir stores sample for additional testing or verification.

Figure 15A:
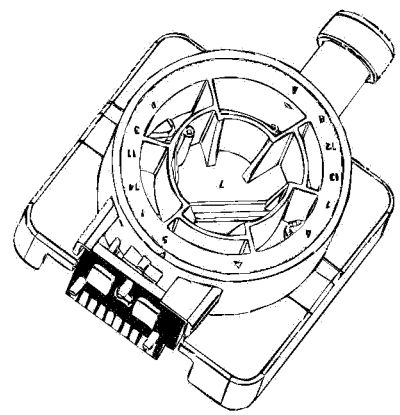
Figure 15B:
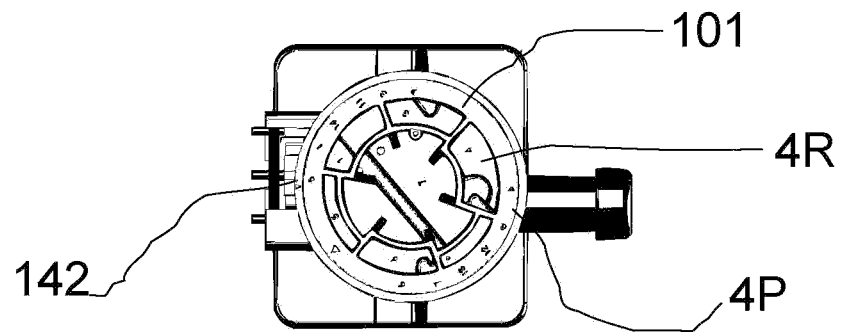
Figure 16A:
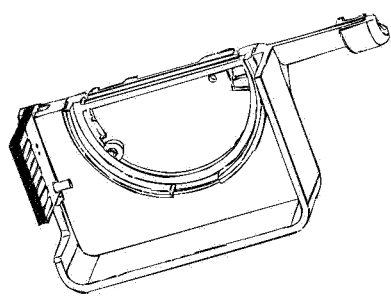
Figure 16B:
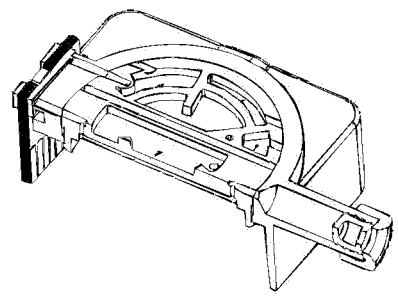
Figure 16C:
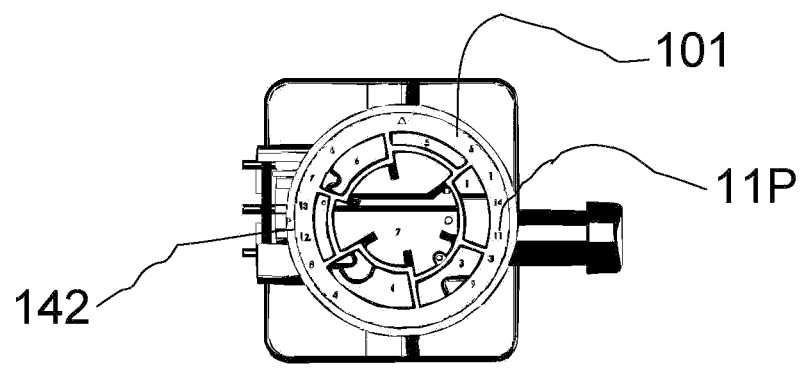

Referring to FIGS. 15A-15B there is shown the reservoir insert 101 positioned such that port 4 is in-line with the syringe molding. Port 4 is in communication with reservoir 4 containing a flush fluid. The flush fluid is drawn from reservoir 4 through port 4 and into the syringe molding. The reservoir insert 101 rotates to port 11 and the plunger pushes the flush fluid into port 11 and to the reaction chamber 142 as shown in FIGS. 16A-16C.

Once completed the rotating valve can be removed and disposed. A fresh rotating valve with the same or unique fluids is then inserted into the detection device.

Figure 17:
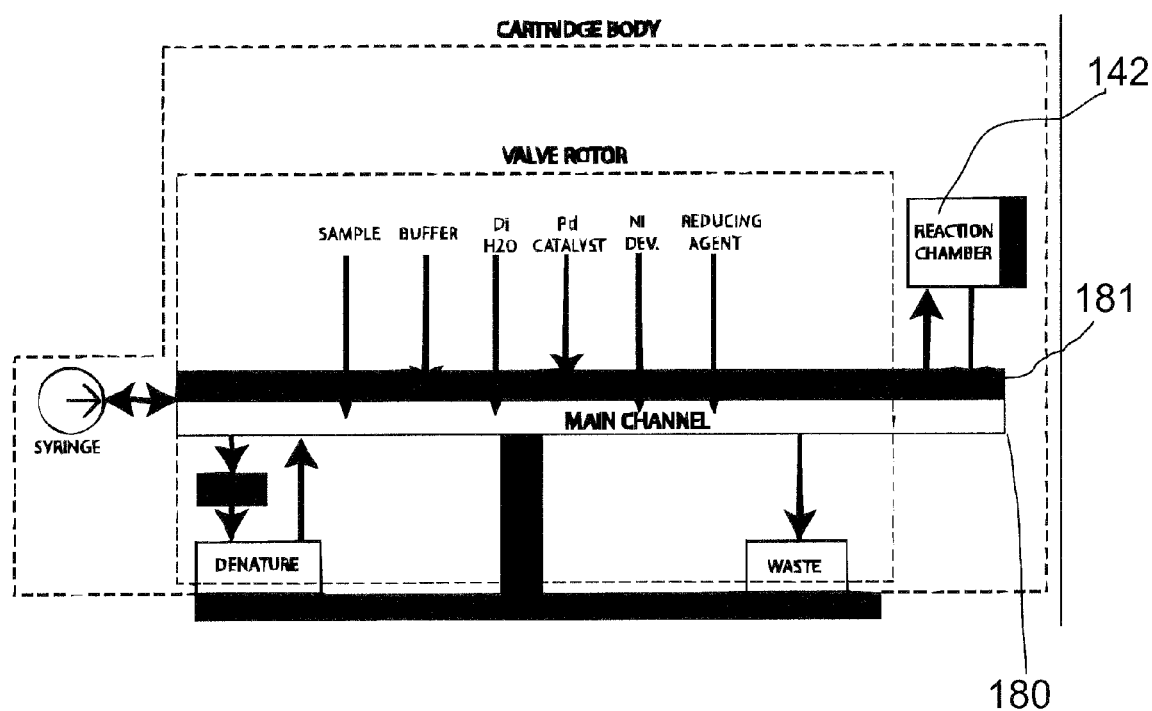
FIG. 17 shows a schematic representation of the rotating valve according to one embodiment.

Referring to FIG. 17 there is shown a schematic of a rotating valve of one embodiment. The reservoir insert contains six fluids in various reservoirs. Five fluids pass from their respective reservoirs into the syringe molding and through the main channel 180 into the reaction chamber 142. One fluid passes from the syringe molding through a secondary channel 181 and into the reaction chamber 142 to prevent any contamination or premature reactions.

Figure 18:
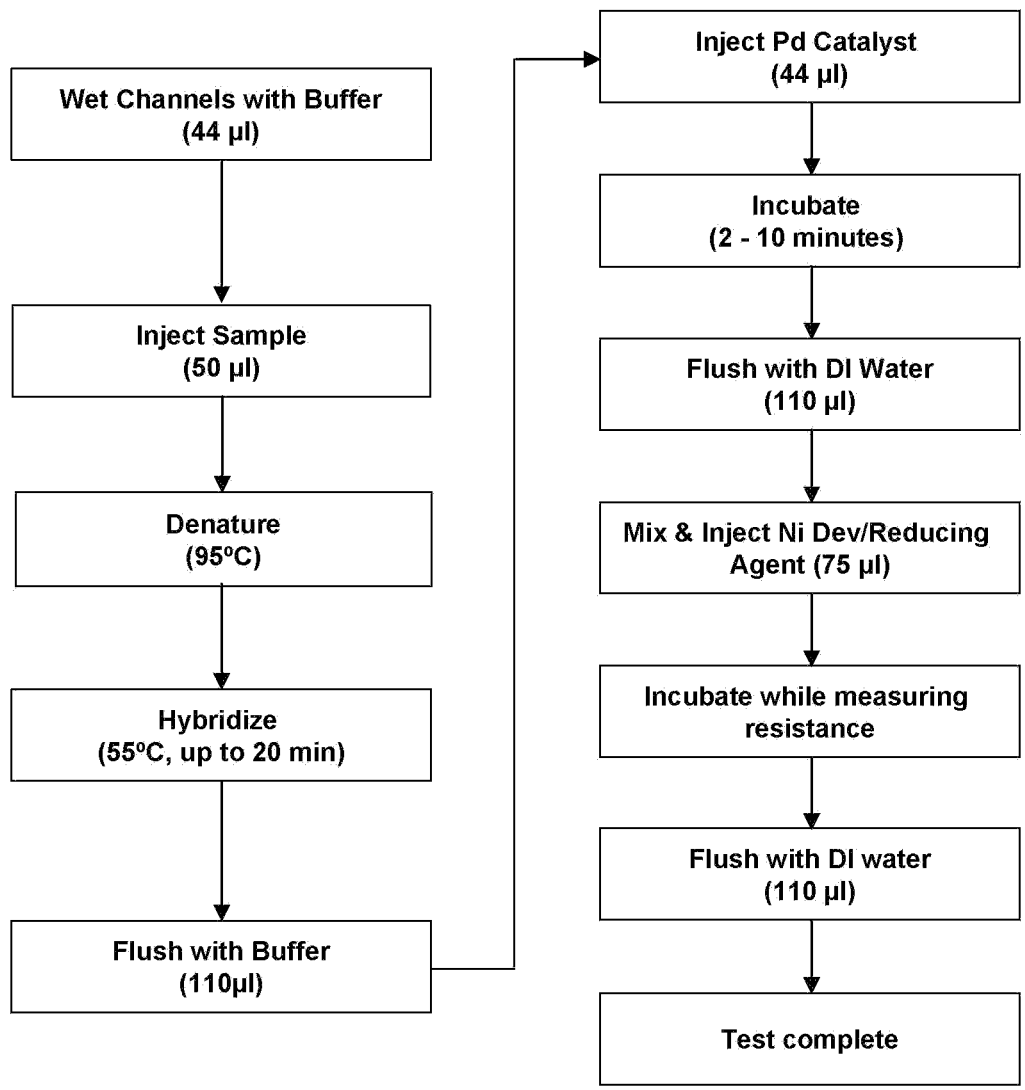
FIG. 18 shows a process flow chart for one use of the rotating valve according to one embodiment.

Referring to FIG. 18 there is shown a process flow according to one embodiment. Once a sample is injected into the sample reservoir and the detection device is activated the testing begins. The channels are first preconditioned with a small amount of buffer. The sample is then transferred from the sample reservoir to the heating reservoir and heated at 95° C. for 5 minutes. The heated sample is then transferred to the reaction chamber to hybridize for 20 minutes. The hybridization process enables the sample to chemically bond with biological probes found on the chip in communication with the reaction chamber. The biological probes specifically bind to target nucleic acid molecules found in the sample as described in U.S. Pat. No. 6,399,303 issued to Connolly on Jun. 4, 2002, which is hereby incorporated by reference. It is understood that a single chip may contain a plurality of distinct and redundant biological probes to increase sensitivity and to test for a variety of target nucleic acid molecules. It is further understood that the rotating valve can be used in any system requiring the manipulation and transport of a plurality of fluids.

After hybridization the sample is flushed with buffer to remove any excess compounds. Optionally a catalyst such as palladium is transferred to the reaction chamber and allowed to incubate for 10 minutes. The remaining catalyst is then flushed with water. A mixture of a reducing agent and metal, such as nickel, are pushed into the reaction chamber. The metal coats the target sample creating a conductor on the chip. The excess non-bonded metal is flushed with water. The resistance across biological probes bonded together by a target sample coated in metal dramatically reduces, indicating the presence of the target sample. The detection device writes the results of the test and the test is complete.

Figure 19A:
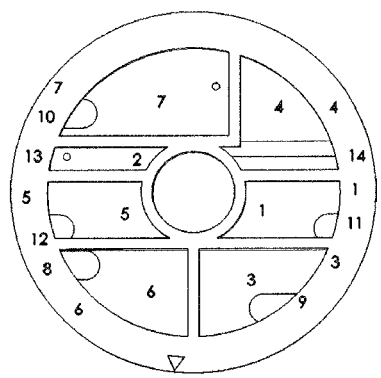
FIGS. 19A-19B show a graphical representation of multi-chamber reservoir insert configurations according to an alternative embodiment.
Figure 19B:
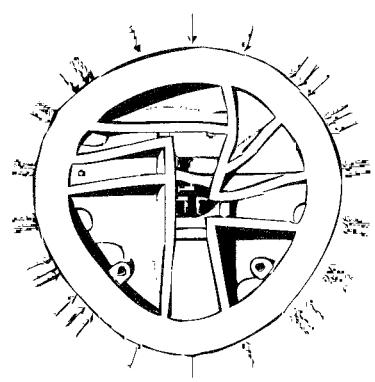

Referring now to FIGS. 19A-19B there is shown a variations of the reservoir insert. The chambers of the insert are shown in a rectangular configuration. Changes to the chamber sizes and shapes can be performed to optimize the particular reagent and waste chambers.

Figure 20A:
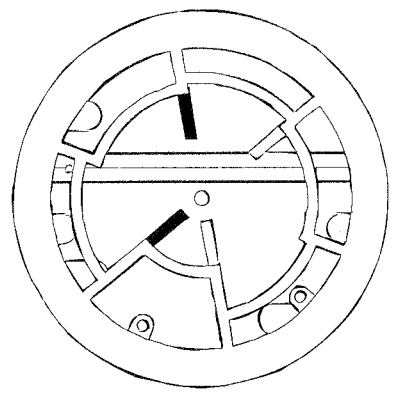
FIGS. 20A-20B show a graphical representation of multi-chamber reservoir insert configurations according to an alternative embodiment.
Figure 20B:
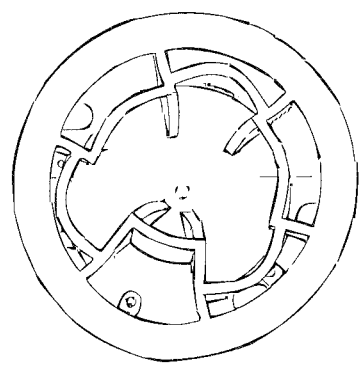

Referring now to FIGS. 20A-20B there are shown variations of the reservoir insert. The chambers of this embodiment are shown to have radial chambers. In one embodiment the chambers are of uniform size and shape around the radius of the insert.

Figure 21A:
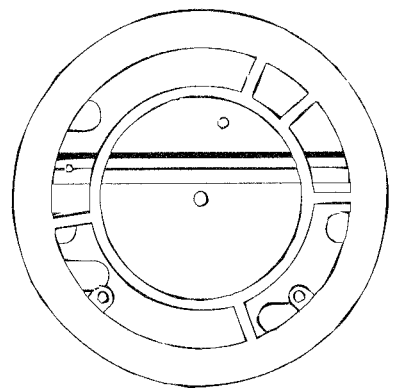
FIGS. 21A-21B show a graphical representation of multi-chamber reservoir insert configurations according to an alternative embodiment.
Figure 21B:
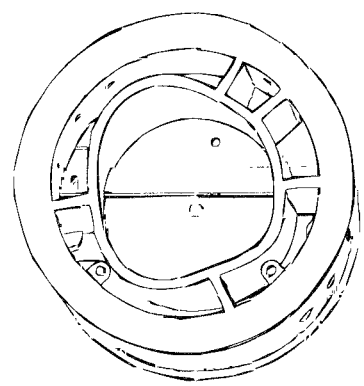

Referring now to FIGS. 21A-21B there are shown variations of the reservoir insert. The chambers are of various sizes along the radius of the insert to house differing amounts of reagents within each chamber. While variations of the insert are shown in the various embodiments, it is understood that any variation of the reservoir insert containing a plurality of ports and reservoirs can be used.

Figure 22:
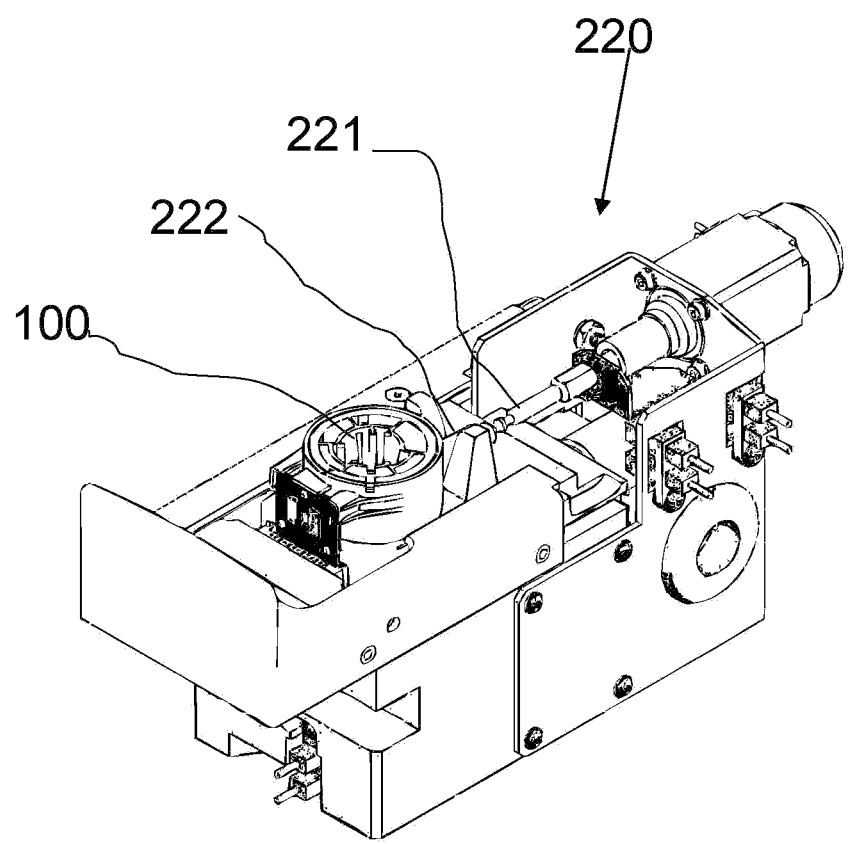
FIG. 22 shows a graphical representation of sampling device containing a rotating valve drive and plunger drive according to one embodiment.

Referring to FIG. 22 there is shown a sampling device having a rotating valve drive and a plunger drive. The rotating valve 100 sets on top of the rotating valve drive. The plunger drive 220 contains a long cylindrical section 221 having a tip 220. The tip 220 connects to the plunger inside of the syringe molding 141. In one embodiment the tip 220 is conical improve contact with the plunger. The plunger drive moves the cylindrical section 221 axially causing the plunger to either pull or push fluids from the reservoirs in the rotating valve 100.

Figure 23:
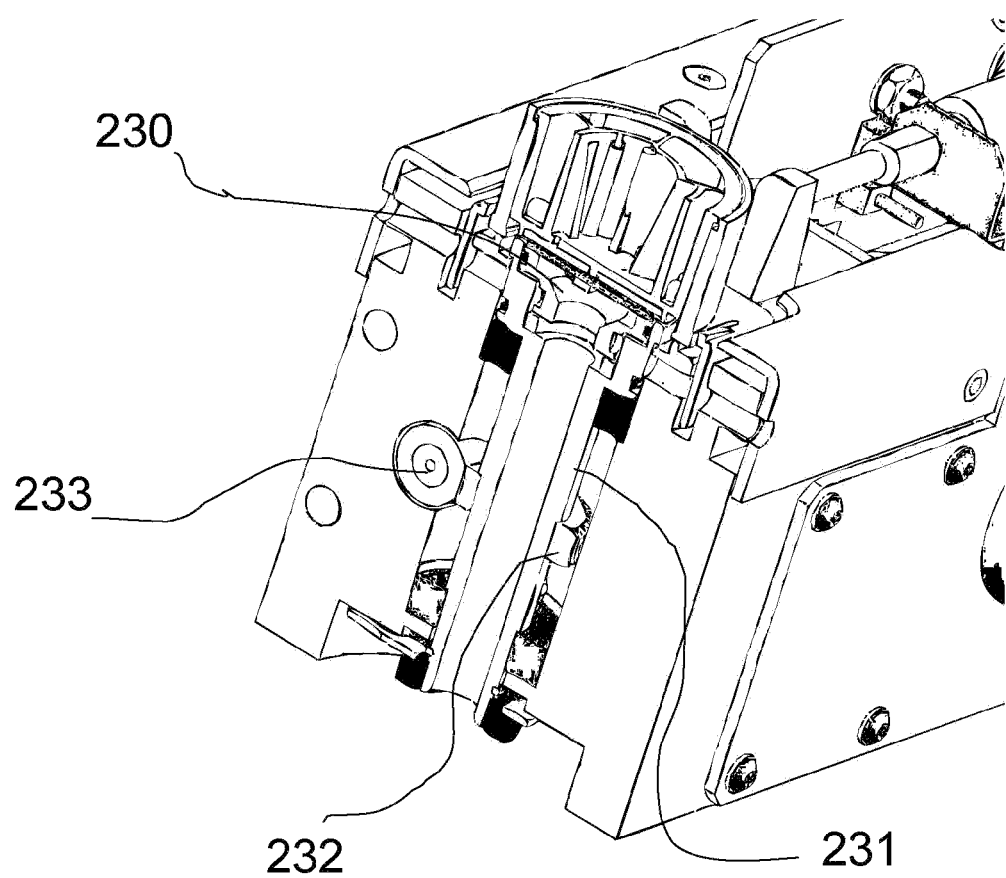
FIG. 23 shows a graphical representation of a rotating valve drive with the rotating valve removed according to one embodiment.

Referring to FIG. 23 there is shown the rotating valve drive according to one embodiment. The rotating valve sets atop the contact surface 230. The contact surface 230 then rotates to position the reservoir insert to the desired location within the rotating valve. In one embodiment the contact surface 230 is part of a drive assembly 231. A worm gear 232 is attached to the drive assembly 231. A worm drive 233 engages the worm gear 232 causing the drive assembly 231 to rotate. It is understood that any suitable means to rotate the reservoir insert can be employed.

Figure 24:
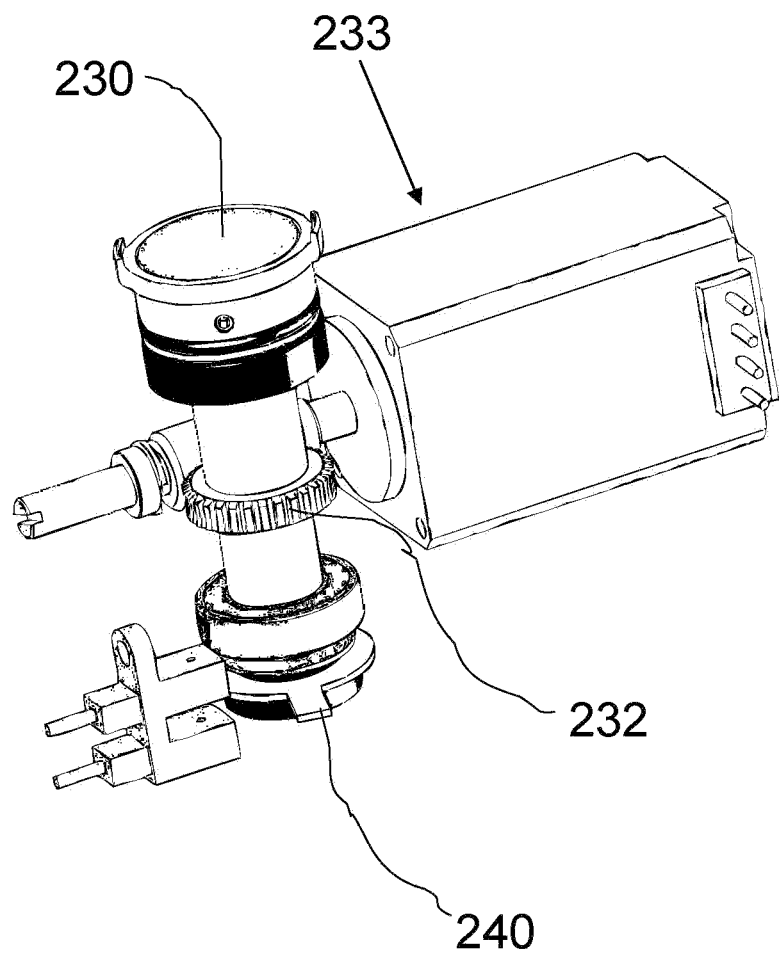
FIG. 24 shows a graphical representation of the stepper motor assembly and worm drive according to one embodiment.

Referring to FIG. 24 there is shown another view of the rotating valve drive. The worm drive 233 is a stepper motor positioned to advance the worm gear 232. A home flag 240 is attached to the drive assembly to zero the device. At any time during fluid sampling the home flag can be zeroed allowing the worm drive 233 to advance the appropriate distance.

Figure 25:
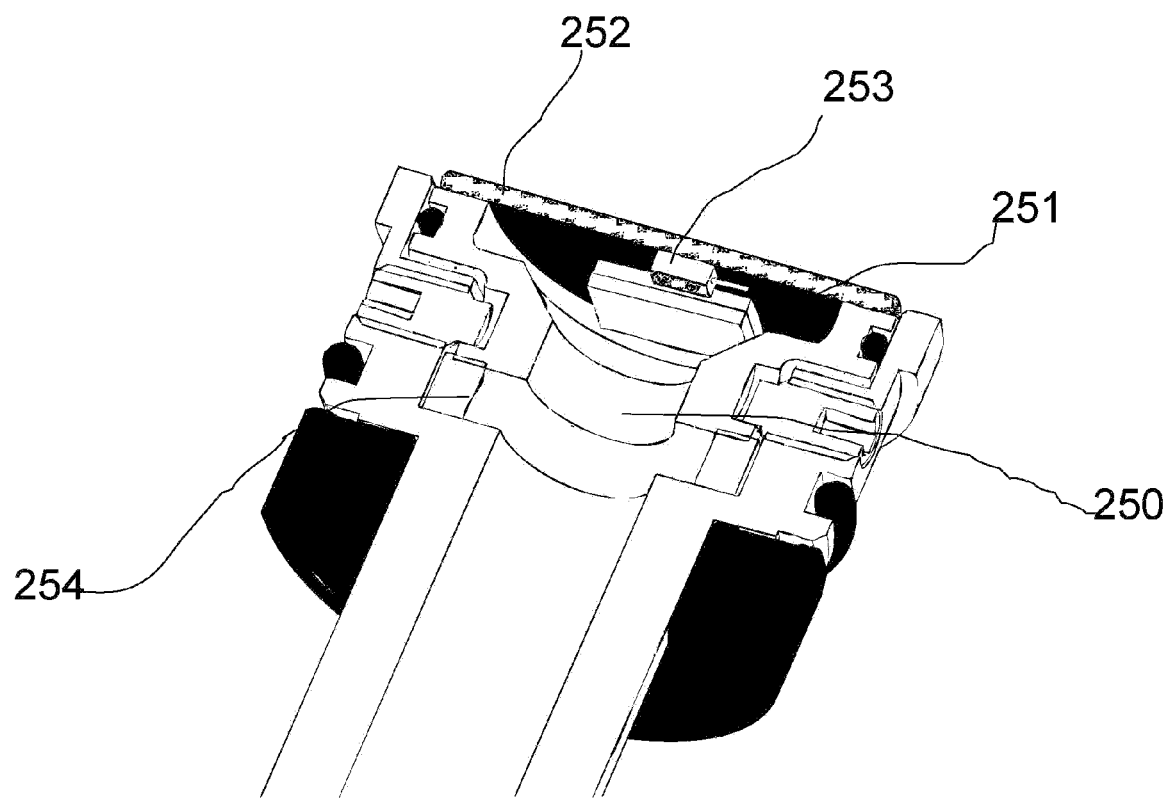
FIG. 25 shows a graphical representation of a the heater according to one embodiment.

Referring to FIG. 25 there is shown the contact surface having a heater. The contact surface is spring loaded to improve contact with the rotating valve. At least one spring 254 is positioned to allow movement of the contact surface. In one embodiment the contact surface contains a heater mount 250 to mount the heating elements. At least one resistor 251 is positioned on the heater mount 250. A heating plate 252 transfers heat from the resistors through the heating plate 252 and to the desired location on the rotating valve. In one embodiment the heating plate is an aluminum heating plate. Optionally, a temperature sensor 253 is positioned near the resistor or heating plate to detect the applied temperature. It is understood that the contact surface (not shown) can be positioned over the heater plate. The contact surface is made from a material that allows an efficient thermal transfer from the heating plate to the rotating valve.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

The invention claimed is:

1. A fluid processing system comprising:
a drive assembly with a longitudinal axis of rotation, the drive assembly comprising a circular contact surface at a first end of the drive assembly, the circular contact surface comprising a heater at a first radial position and a magnet at a second radial position;
a cartridge body disposed proximate the first end of the drive assembly and non-rotatably disposed on the circular contact surface, the cartridge body comprising an inner cylindrical surface, a syringe molding extending from an outer surface of the cartridge body, a syringe port in the syringe molding that connects the inner cylindrical surface to the outer surface, the inner cylindrical surface and the outer surface being opposite each other and parallel the longitudinal axis of rotation of the drive assembly; and
a reservoir insert rotatably disposed to the inner cylindrical surface and operatively connected to the drive assembly such that rotation of the drive assembly causes the reservoir insert to rotate within the cartridge body, wherein the reservoir insert comprises
a cylindrical sidewall with a plurality of fluid ports disposed on an outside surface thereof including reservoir fluid ports, a first through-channel fluid port and a second through-channel fluid port, each fluid port being a first distance from a bottom of the reservoir insert such that each fluid port may be selectively aligned with the syringe port, the cylindrical sidewall further comprising a plurality of relief ports disposed on the outside surface and above the plurality of fluid ports,
a plurality of reservoirs within a perimeter defined by the cylindrical sidewall, each one of the plurality of reservoirs being fluidly connected to one reservoir fluid port of the plurality of fluid ports and one relief port of the plurality of relief ports, and
a through channel extending along the bottom of the reservoir insert, the through channel being fluidly connected to the first through-channel fluid port and the second through-channel fluid port at respective ends of the through channel, the through channel being selectively positionable proximate the heater or the magnet by rotation of the reservoir insert such that contents of the through channel can experience heat from the heater or a magnetic field from the magnet.

2. The system as recited in claim 1, wherein the plurality of relief ports are disposed above the bottom of the reservoir insert by a second distance that is greater than the first distance.

3. The system as recited in claim 1, further comprising a worm drive operatively connected to the drive assembly by a worm gear such that the actuation of the worm drive causes the drive assembly to rotate about the longitudinal axis of rotation.

4. The system as recited in claim 1, wherein the cartridge body further comprises a reaction chamber disposed on the outer surface of the cartridge body.

5. The system as recited in claim 4, wherein the reaction chamber comprises a chip having biological microprobes, the chip forming a wall of the reaction chamber.

6. The system as recited in claim 1, further comprising a plunger fluidly connected to the syringe port.

7. The system as recited in claim 6, wherein the syringe port extends perpendicularly from the outer surface of the cartridge body such that the syringe port may be selectively aligned with one fluid port of the plurality of fluid ports.

8. The system as recited in claim 1, further comprising a film seal to retain fluids within the plurality of reservoirs.

9. The system as recited in claim 1, further comprising a temperature sensor disposed in the circular contact surface proximate the heater.

10. The system as recited in claim 1, wherein the circular contact surface further comprises an ultrasonic disruptor at a central position, and the plurality of reservoirs further comprises at least one sample reservoir that is located directly above the ultrasonic disruptor.

11. The system as recited in claim 10, further comprising a temperature sensor disposed in the circular contact surface proximate the heater.

12. The system as recited in claim 10, wherein each one of the plurality of reservoirs is disposed above the circular contact surface.

13. The system of claim 11, wherein the at least one sample reservoir contains a plurality of disrupting objects.

14. The system of claim 12 wherein the disrupting objects are glass beads.

15. The system as recited in claim 1, wherein the circular contact surface further comprises an ultrasonic source at a central position, and the plurality of reservoirs further comprises at least one sample reservoir that is located directly above the ultrasonic source.

* * * * *